( 12 ) United States Patent
Calusinska et al.

(10) Patent No.: US 11,293,036 B2
(45) Date of Patent: Apr. 5, 2022

US011293036B2

(54) BIOLOGICAL AGENT FOR ENRICHMENT OF ANAEROBIC DIGESTION REACTORS, METHOD OF PREPARING SUCH BIOLOGICAL AGENT AND BIO-AUGMENTATION PROCESS WITH SAID AGENT

(71) Applicant: LUXEMBOURG INSTITUTE OF SCIENCE AND TECHNOLOGY, Esch-sur-Alzette (LU)

(72) Inventors: Magdalena Calusinska, Halanzy (BE); Philippe Delfosse, Bettembourg (LU); Xavier Goux, Metz (FR); Sébastien Lemaigre, Messancy (BE)

(73) Assignee: LUXEMBOURG INSTITUTE OF SCIENCE AND TECHNOLOGY, Esch-sur-Alzette (LU)

( * ) Notice: Subject to any disclaimer, the term of this patent is extended or adjusted under 35 U.S.C. 154(b) by 342 days.

(21) Appl. No.: 16/469,497

(22) PCT Filed: Dec. 14, 2017

(86) PCT No.: PCT/EP2017/082864
§ 371 (c)(1),
(2) Date: Jun. 13, 2019

(87) PCT Pub. No.: WO2018/122000
PCT Pub. Date: Jul. 5, 2018

(65) Prior Publication Data
US 2020/0131541 A1   Apr. 30, 2020

(30) Foreign Application Priority Data
Dec. 27, 2016   (LU) .......................................... 93402

(51) Int. Cl.
*C12P 5/02*   (2006.01)
*C12N 1/20*   (2006.01)
*C02F 3/28*   (2006.01)
*C12P 39/00*   (2006.01)
*C12R 1/01*   (2006.01)

(52) U.S. Cl.
CPC .............. *C12P 5/023* (2013.01); *C12N 1/205* (2021.05); *C02F 3/28* (2013.01); *C12P 39/00* (2013.01); *C12R 2001/01* (2021.05)

(58) Field of Classification Search
None
See application file for complete search history.

(56) References Cited

U.S. PATENT DOCUMENTS

2017/0314045 A1   11/2017 Esteves et al.

OTHER PUBLICATIONS

Klocke, Michael, et al. "Microbial community analysis of a biogas-producing completely stirred tank reactor fed continuously with fodder beet silage as mono-substrate." Systematic and applied microbiology 30.2 (2007): 139-151. (Year: 2007).*
Tang, Yueqin, et al. "Microbial community analysis of mesophilic anaerobic protein degradation process using bovine serum albumin (BSA)-fed continuous cultivation." Journal of Bioscience and Bioengineering 99.2 (2005): 150-164. (Year: 2005).*
Janda, J. Michael, and Sharon L. Abbott. "16S rRNA gene sequencing for bacterial identification in the diagnostic laboratory: pluses, perils, and pitfalls." Journal of clinical microbiology 45.9 (2007): 2761-2764. (Year: 2007).*
Eric Pelltier et al.: ""Candidatus Cloacamonas Acidaminovorans": Genome Sequence Reconstruction Provides a First Glimpse of a New Bacterial Division." vol. 190, No. 7; Jan. 14, 2008.
Delphine Riviere et al.: "Towards the definition of a core of microorganisms involved in anaerobic digestion of sludge." Feb. 26, 2009; The ISME Journal (2009).
Klocke et al: "Microbial community analysis of a biogas-producing completely stirred tank reactor fed continuously with fodder beet silage as mono-substrate", Systematic and Applied Microbiol, Urban & Fischer, Amsterdam, NL, Feb. 8, 2007.
Ext. Mar. 2, 2006 (Mar. 2, 2006), "Uncultured bacterium clone ATB-KM1360 16S ribosomal RNA gene, partial sequence.", retrieved from EBI accession No. EM STD:DQ390306.
Ext. Mar. 2, 2006 (Mar. 2, 2006), "Uncultured bacterium clone ATB-KM1340 16S ribosomal RNA gene, partial sequence.", retrieved from EBI accession No. EM STD:DQ390298.
Zhang Jie et al: "Bioaugmentation with an acetate-type fermentation bacteriumAcetobacteroides hydrogenigenesimproves methane production from corn straw", Bioresource Technology.
Xavier Goux et al: "Microbial community dynamics in replicate anaerobic digesters exposed sequentially to increasing organic loading rate, acidosis, and process recovery", Biotechnology for Biofuels Aug. 19, 2015.
Yvonne Stolze et al: "Identification and genome reconstruction of abundant distinct taxa in microbiomes from one thermophilic and three mesophilic production-scale biogas plants", Biotechnology for Biofuels Jul. 26, 2016.
Yueh-Fen Li et al: "Spatial and temporal variations of microbial community in a mixed plug-flow loop reactor fed with dairy manure : Microbiome in a mixed plug-flow loop reactor", Microbial Biotechnology Apr. 1, 2014.
Linn Sol Li et al: "A metagenomi c study of the microbial communities in four parallel biogas reactors", Biotechnology for Biofuels, Biomed Central Ltd. Oct. 14, 2014.
International Search Report dated Aug. 29, 2017.
International Search Report dated Apr. 24, 2018.

* cited by examiner

*Primary Examiner* — Robert J Yamasaki
(74) *Attorney, Agent, or Firm* — Ipsilon USA, LLP

(57) ABSTRACT

Biological agent for bio-augmentation of an anaerobic digestion reactor, named first anaerobic digestion reactor, comprising a mixture of microorganisms including at least 10% of relative abundance in said mixture, of a unique *Cloacimonetes* sp. This agent is prepared by enrichment of a biological sample in a separate reactor fed with carbohydrate-rich substrate and oxygenated gas.
Said agent comprising this unique *Cloacimonetes* sp. is able to restore and stabilize the biogas production of an anaerobic digestion reactor after acidosis, in a very short time.

19 Claims, 4 Drawing Sheets

Specification includes a Sequence Listing.

SEQUENCE LISTING

```
<160> NUMBER OF SEQ ID NOS: 6

<210> SEQ ID NO 1
<211> LENGTH: 499
<212> TYPE: DNA
<213> ORGANISM: Cloacimonetes sp.

<400> SEQUENCE: 1
aaaggaattg acgggggccc gcacaagcgg tggagcatgt ggtttaattc gaagcaacgc      60
gaagaacctt acccggtctt gacatccgag ggatccctca gagatggggg agtgccggct     120
agccggaact tcgagacagg tgctgcatgg ctgtcgtcag ctcgtgtcgt gagatgttgg     180
gttaagtccc gcaacgagcg caacccctgc ttccagttac catcattaag ttggggactc     240
tggaaggacc gctgcggtaa caacgcagag gaagatgggg acgatgtcaa gtcatcatgg     300
tccttatgac cggggctaca cacgtgctac aatggtagtt acagagggat gcgaaggggt     360
gacctggagc taatctctta aaagctgcca cagttcggat tgaggtctgc aactcgacct     420
catgaagcag gaatcgctag taatcgcgca acatcatggc gcggtgaata cgttcccggg     480
ccttgtacac accgcccgt                                                  499

<210> SEQ ID NO 2
<211> LENGTH: 18
<212> TYPE: DNA
<213> ORGANISM: Artificial Sequence
<220> FEATURE:
<223> OTHER INFORMATION: primer_S

<400> SEQUENCE: 2
actcaaakga atwgacgg                                                    18

<210> SEQ ID NO 3
<211> LENGTH: 15
<212> TYPE: DNA
<213> ORGANISM: Artificial Sequence
<220> FEATURE:
<223> OTHER INFORMATION: primer_S

<400> SEQUENCE: 3
acgggcggtg tgtrc                                                       15

<210> SEQ ID NO 4
<211> LENGTH: 20
<212> TYPE: DNA
<213> ORGANISM: Artificial Sequence
<220> FEATURE:
<223> OTHER INFORMATION: primer_F

<400> SEQUENCE: 4
ccttacccgg tcttgacatc                                                  20

<210> SEQ ID NO 5
<211> LENGTH: 20
<212> TYPE: DNA
```

```
<213> ORGANISM: Artificial Sequence
<220> FEATURE:
<223> OTHER INFORMATION: primer_R

<400> SEQUENCE: 5
gtaactggaa gcaggggttg                                            20

<210> SEQ ID NO 6
<211> LENGTH: 14
<212> TYPE: DNA
<213> ORGANISM: Artificial Sequence
<220> FEATURE:
<223> OTHER INFORMATION: probe

<400> SEQUENCE: 6
cgagggatcc ctca                                                  14
```

BIOLOGICAL AGENT FOR ENRICHMENT OF ANAEROBIC DIGESTION REACTORS, METHOD OF PREPARING SUCH BIOLOGICAL AGENT AND BIO-AUGMENTATION PROCESS WITH SAID AGENT

RELATED APPLICATION

This application is a National Phase of PCT/EP2017/082864 filed on Dec. 14, 2017, which claims the benefit of priority from Luxembourg Patent Application No. 93402, filed on Dec. 27, 2016, the entirety of which are incorporated by reference.

The substitute sequence listing entitled "sequencelisting-substituteJanuary162020" created on Jan. 16, 2020, and being 2.01 KB (2,066 bytes) in size, is hereby incorporated by reference.

FIELD OF THE INVENTION

The present invention relates to anaerobic digestion reactors, in particular to a process for improving or restoring the performance of said rectors.

The invention also relates to a biological agent for enrichment of said anaerobic digestion reactors, and to the method of preparing such biological agent.

STATE OF THE ART

Acidification (also named acidosis) of anaerobic digestion reactors for biogas (especially methane) production is the most common process failure that can take place in many digesters and for which the biogas world seeks solutions for quickly and efficiently recovering the digestion process.

Volatile fatty acids (VFAs), such as acetic acid and propionic acid, are constantly reported at elevated concentrations in acidified anaerobic digestion reactors, characterized by low methane production. As a consequence, acidosis leads to important losses in revenue, therefore it is important to prevent it and on the other hand to quickly restart the process once the acidosis takes place.

Up to now, two types of solutions have been brought up to deal with the acidosis problem.

The first solution is a chemical treatment, wherein an alkaline agent, such as quick lime (CaO), sodium hydroxide (NaOH) or calcium hydroxide ($Ca(OH)_2$), is added to the reactor medium. This resolves only temporarily the pH, and the metal included in the alkali can cause process inhibition in the reactor or can unwittingly accumulate in agricultural soils when the process residue (biogas digestate) is spread as organic fertilizer.

Another solution is to add beneficial microorganism(s) to improve or re-establish the performance of anaerobic digestion reactors: this is the basis of bio-augmentation targeting increased process efficiency to the reactor medium. These bio-augmentation techniques use a specific synthetic composition comprising a strain or an artificial mixture of a few strains of microorganisms which has been previously obtained and maintained in an isolated culture, enriched to degrade a specific substrate. For instance, adding propionate-utilizing enrichment cultures that can convert acetate and propionate to methane may lead to improved digestion.

Tale et al. (*Water research,* 70:138-147, 2015) describes such bio-augmentation techniques starting with samples from an anaerobic digester treating brewery wastewater enriched each day in propionate. These enriched cultures were subsequently used to bio-augment organically overloaded digesters. However bio-augmentation realized with a single strain or with an artificial mixture of a few strains of cultivable microorganisms usually results in transient or weak improvement.

AIM OF THE INVENTION

Consequently, a first aim of the invention is to provide a composition or agent to be added to an anaerobic digestion reactor to reduce acidosis in anaerobic digestion reactors in order to improve or re-establish the performance of said reactor (biogas or methane production), without adding alkaline substances.

Another aim of the invention is to provide a composition or agent to also prevent acidosis in anaerobic digestion reactors in order to improve the performance of said reactor (biogas or methane production).

Still another aim of the present invention is to provide a composition or agent to increase the production yield of an anaerobic digestion reactor.

Still another aim of the invention is to provide a method for reducing costs for managing and maintaining the working of an anaerobic digestion reactor.

SUMMARY OF THE INVENTION

During the research work of the inventors, it has now been found, surprisingly, that the presence of a specific microorganism would help to obtain the required above results.

Consequently, the present invention relates to a biological agent for bio-augmentation of an anaerobic digestion reactor, named first anaerobic digestion reactor, comprising a mixture of microorganisms including at least 10%, preferably at least 25%, more preferably 30-50%, of abundance of a unique *Cloacimonetes* sp. of the total microorganisms abundance in said mixture, said unique *Cloacimonetes* sp. having a 16S rRNA gene signature comprising the following specific sequence:

```
                                           (SEQ ID NO: 1)
AAAGGAATTGACGGGGGCCCGCACAAGCGGTGGAGCATGTGGTTTAATTC

GAAGCAACGCGAAGAACCTTACCCGGTCTTGACATCCGAGGGATCCCTCA

GAGATGGGGGAGTGCCGGCTAGCCGGAACTTCGAGACAGGTGCTGCATGG

CTGTCGTCAGCTCGTGTCGTGAGATGTTGGGTTAAGTCCCGCAACGAGCG

CAACCCCTGCTTCCAGTTACCATCATTAAGTTGGGGACTCTGGAAGGACC

GCTGCGGTAACAACGCAGAGGAAGATGGGGACGATGTCAAGTCATCATGG

TCCTTATGACCGGGGCTACACACGTGCTACAATGGTAGTTACAGAGGGAT

GCGAAGGGGTGACCTGGAGCTAATCTCTTAAAAGCTGCCACAGTTCGGAT

TGAGGTCTGCAACTCGACCTCATGAAGCAGGAATCGCTAGTAATCGCGCA

ACATCATGGCGCGGTGAATACGTTCCCGGGCCTTGTACACACCGCCCGT.
```

The inventors have discovered, surprisingly, said *Cloacimonetes* sp. having a 16S rRNA gene signature comprising above sequence (SEQ ID NO:1) is able to restore the biogas production of an anaerobic digestion reactor after acidosis, in a very short time, as can be seen in the example part of the description.

This biological agent could also comprise other microorganisms selected from the following phyla: Bacteroidetes, Firmicutes, Proteobacteria, Chloroflexi, Synergistetes, and/or Microgenomates (OP11).

Said unique *Cloacimonetes* sp. is an anaerobic organism and above microorganisms are also mainly anaerobic microorganisms.

Said agent of the invention may be in the form of a water-based composition, in liquid or frozen state, or a lyophilized composition. A water-based composition (fresh or frozen), presents the advantage that said mixture comprising the unique *Cloacimonetes* sp. is directly active and will have less problem to compete with the existing microbes and will thus surely and rapidly establish in the reactor.

A preservative compound may be added when necessary, but the biological agent of the present invention can be used as itself, without adding any other ingredient or active substance.

The present invention also relates to a method for preparing the biological agent/composition described above, comprising the following steps:

i) identifying a suitable biological sample containing a unique *Cloacimonetes* sp., having a 16S rRNA gene signature comprising the above sequence (SEQ ID NO:1), in a relative abundance of at least 0.01%, preferably 0.05%, of the total microorganisms abundance of the sample, ii) inoculating the reactor medium of a second anaerobic digestion reactor with the identified biological sample containing said unique *Cloacimonetes* sp., iii) feeding said anaerobic digestion reactor medium with a carbohydrate-rich (preferably pectin/cellulose/lingo-cellulose-rich) substrate at high organic loading rates (OLR) and optionally supplemented with organic acid(s), preferably acetic and/or propionic acid(s), or salts thereof, iv) mixing said reactor at regular time intervals and injecting oxygenated gas, v) monitoring the enrichment of the reactor medium in said unique *Cloacimonetes* sp. until the abundance of *Cloacimonetes* sp. reaches at least 10%, preferably 25%, more preferably 30-50%, of the total microorganisms abundance in said mixture reactor medium, to obtain the water-based biological agent/composition, and vi) optionally freezing, concentrating or lyophilizing the water-based biological composition to preserve said biological agent/composition.

The starting biological sample is thus enriched in the unique *Cloacimonetes* sp. having a 16S rRNA gene signature comprising SEQ ID NO:1.

The starting biological sample may be a sludge or slurry issued from waste water treatment plant, or a sample issued from the environment (for instance sediment, soil, lake, ocean; etc. . . . ), or may be issued from an anaerobic digestion reactor fed with waste water sludge, or agricultural residues, containing a relative abundance of at least 0.01%, preferably 0.05% of said unique *Cloacimonetes* sp.

Advantageously, said biological sample is a water-based sample.

The feeding substrate is a carbohydrate-rich substrate, preferably a cellulose-rich or pectin-rich or lignocellulose-rich substrate, for example a vegetable waste chosen among organic domestic and/or industrial food waste, such as sugar beet pulp, fruit pulp, cereal residues, potatoes. Said list is not limitative.

By high organic rate is hereby meant an organic load above the initial loading rate of said second anaerobic digestion reactor. For instance the high organic loading rate (ORL) of this second anaerobic digestion reactor is in the range of 4-10 kg volatile solids $VS.m^{-3}.d^{-1}$, preferably in the range 6-8 kg $VS.m^{-3}.d^{-1}$.

Supplementation in organic acid(s) is only optional: enrichment of the sample in said unique *Cloacimonetes* sp. can be obtained without addition of organic acid(s) in the feeding substrate.

The oxygenated gas injected at time intervals in the reactor may be a biogas enriched with oxygen, pure oxygen, or air, or air enriched with oxygen. Although the microorganisms present in the biological starting sample, including said unique *Cloacimonetes* sp, are mainly anaerobic microorganisms, injection of oxygenated gas is beneficial to the enrichment in said unique *Cloacimonetes* sp of the biological sample. Enrichment of the reactor medium in said unique *Cloacimonetes* sp. may reach 30-50% of relative abundance of *Cloacimonetes* sp. of the total microorganisms abundance in said mixture reactor medium.

Optionally, a preservative agent may be added to the water-based composition obtained at step v).

The present invention also relates to a process for preventing or reducing acidosis in an anaerobic digestion reactor, such as an anaerobic digestion reactor producing methane, in order to improve or re-establish the performance of said reactor (for instance methane production), comprising bio-augmenting said reactor with the biological agent of the present invention prepared according to the above method.

Advantageously, the process comprises solely the bio-augmentation of said biological agent of the present invention prepared according to the above method. Bio-augmenting such anaerobic digestion reactors with said biological agent/composition of the invention is therefore a very promising solution to improve the digestion and prevent acidosis or to quickly restart the digestion process.

The present invention also relates to several different uses of the above process:

increasing the organic loading rate (ORL), preferably up to 10-12 kg $VS.m^{-3}.d^{-1}$, of an anaerobic digestion reactor;

increasing the organic loading rate (ORL) of an anaerobic digestion reactor producing methane, preferably under mesophilic conditions;

increasing the production yield of an anaerobic digestion reactor;

increasing the methane production yield, preferably up to 2 to 3 NL $CH_4.L^{-1}.d^{-1}$, of an anaerobic digestion reactor producing methane, preferably under mesophilic conditions.

FIGURES

The invention will be further described in the below embodiments given with reference to the accompanying drawings, in which.

Figure 3:
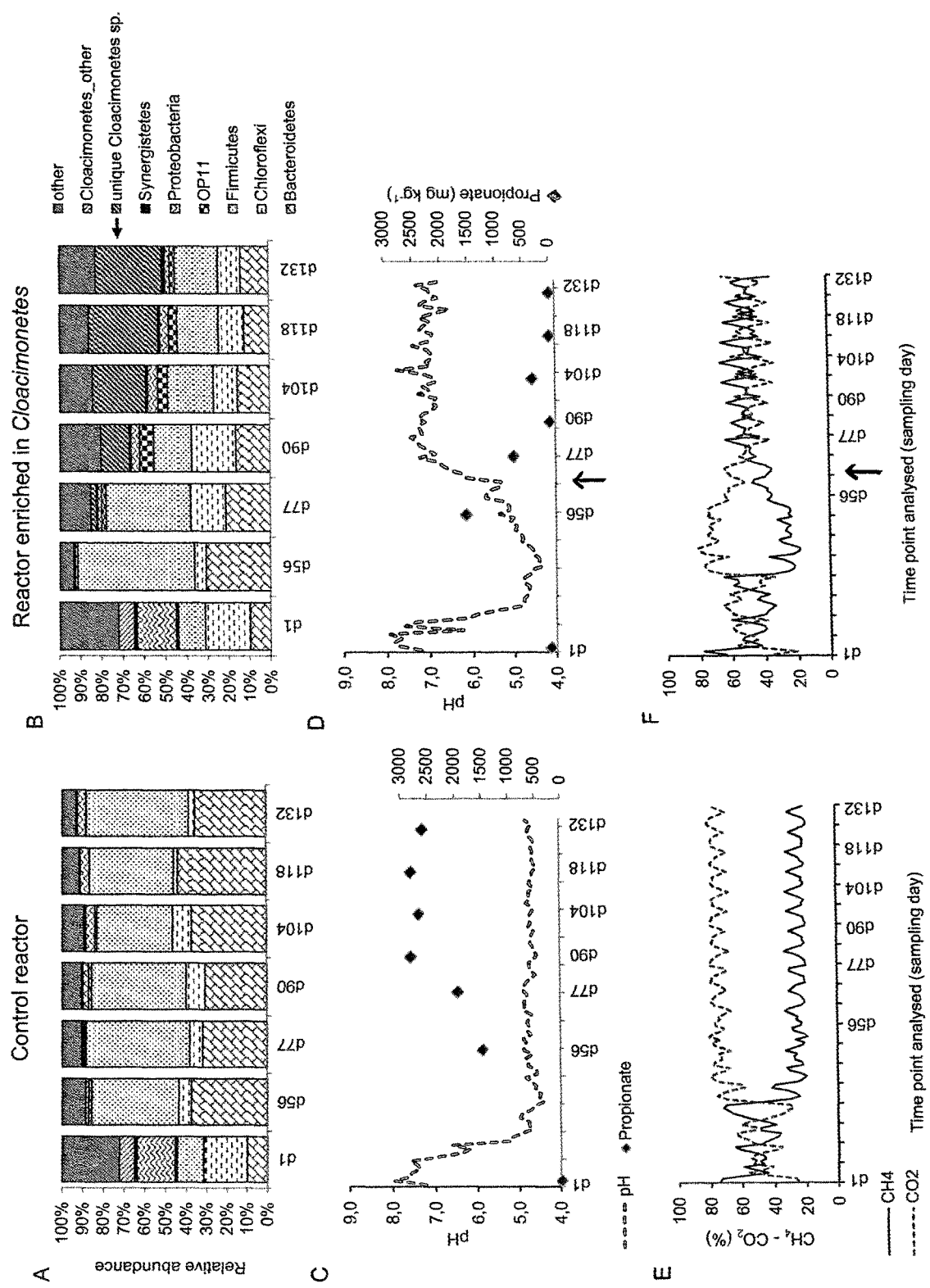
Figure 4:
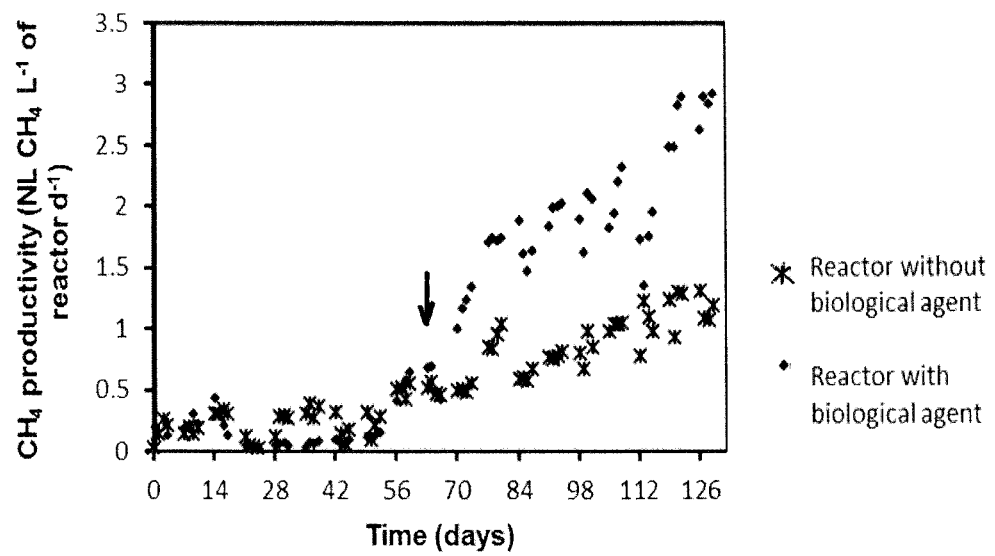
Figure 6:
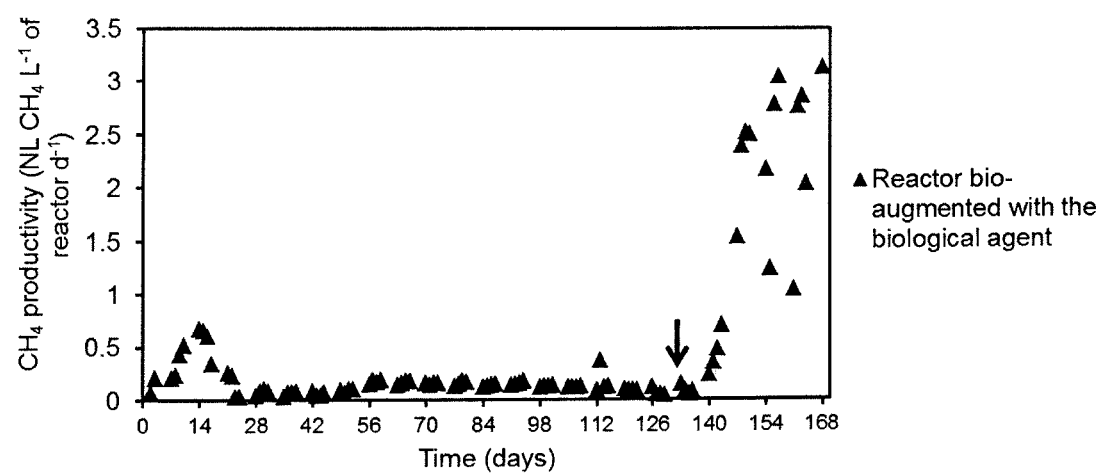
Figure 5:
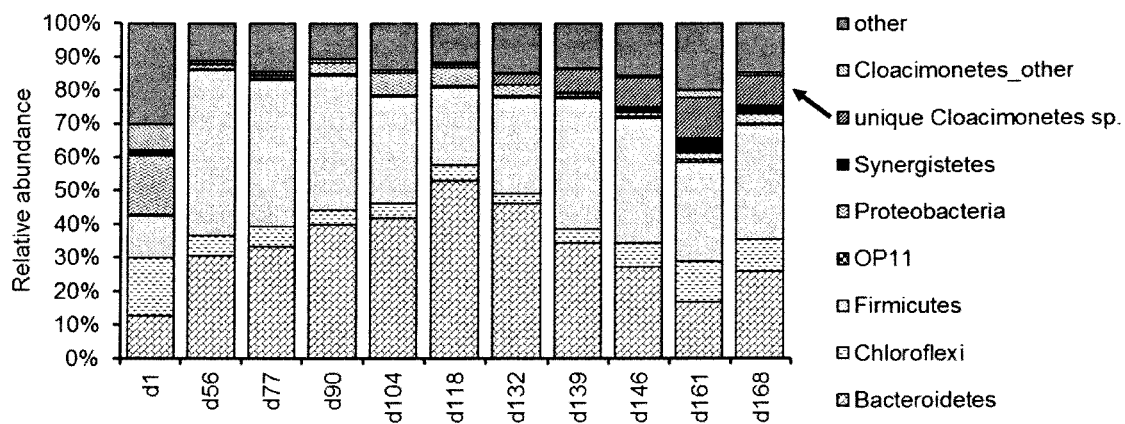
Figure 5:
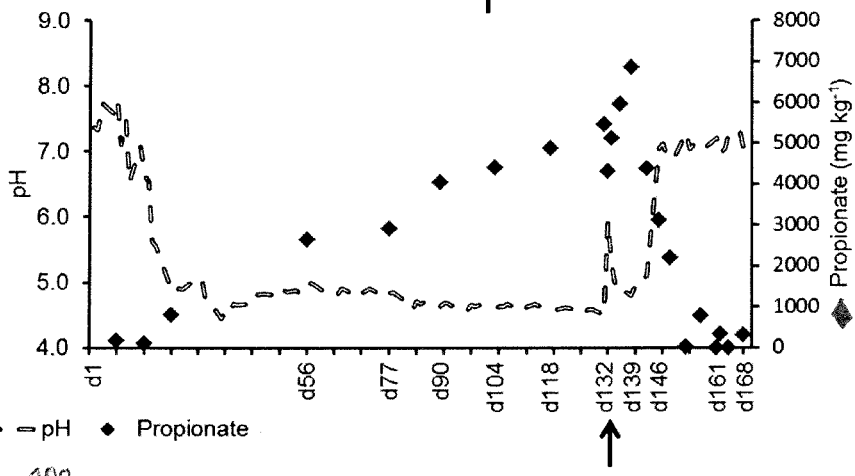
Figure 5:
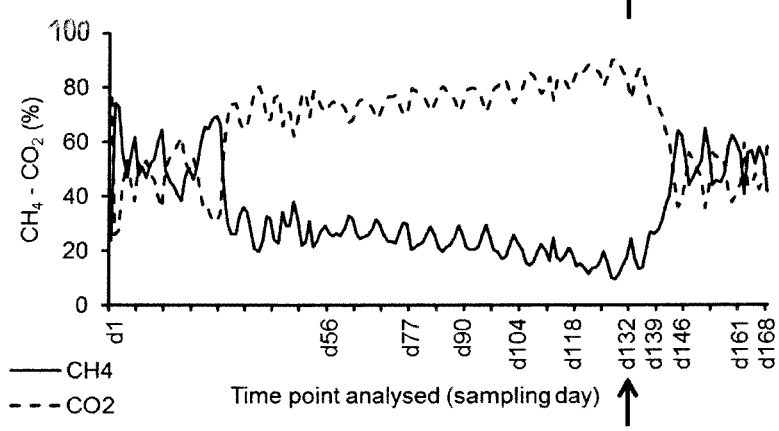

FIG. 3 shows the behavior of an anaerobic digestion reactor augmented in the biological agent of the invention (an arrow indicates start of bio-augmentation) comprising unique *Cloacimonetes* sp. (diagrams B, D and F) compared to a control reactor without bio-augmentation (diagrams A, C and E) (diagrams A and B: relative abundance of microorganisms, C and D: pH values and propionate concentration, E and F: % in $CH_4$ and $CO_2$ in the biogas) during 132 days;

FIG. 4 is a graph showing the methane productivity of anaerobic digestion reactors with and without augmentation of the biological agent of the invention (an arrow indicates start of bio-augmentation);

FIG. 5 shows the behavior of another anaerobic digestion reactor augmented in the biological composition of the invention comprising unique *Cloacimonetes* sp. (the beginning of the bio-augmentation is indicated with an arrow), (diagram A: relative abundance of microorganisms, B: pH values and propionate concentration, C: % in $CH_4$ and $CO_2$ in the biogas) during 168 days; and FIG. 6 is a graph showing the methane productivity of the anaerobic digestion reactor of FIG. 5, augmented in the biological composition of the invention comprising unique *Cloacimonetes* sp. (the beginning of the bio-augmentation is indicated with an arrow).

EXAMPLES

Material and Methods

Biological Sample

Biological agent originates from an anaerobic slurry originating from an anaerobic reactor fed with waste water sludge, and having the following specifications: pH range from 5 to 8, dry matter content in a range of 2 to 5 mass %, alkalinity in the range of 4000 to 8000 mg of CaCO3 per L of sludge.

Determination of the Unique *Cloacimonetes* sp. in the Biological Starting Sample and in the Biological Agent of the Invention.

The detection can be done using either of the two methods specified below:

Method 1: 16S rRNA gene amplicon high-throughput sequencing as described in Goux et al. 2016 (DOI: 10.1016/j.biortech.2016.04.040).

After DNA extraction, using commonly available DNA extraction kits from environmental samples, a PCR reaction mixture is prepared using modified primers S-D-Bact-0909-a-S-18 and S-*-Univ-1392-a-A-15 (sequences as described below), specifically targeting bacterial 16S rRNA gene. As modification, the Nextera XT® transposase sequence (Illumina Inc., San Diego, USA) was included in the 5' end of the forward and reverse primer, and additional four N (i.e. four random nucleotides) were added in the forward primer to increase the nucleotide diversity.

```
primer S-D-Bact-0909-a-S-18 (5→3)
                                   (SEQ ID NO: 2)
ACTCAAAKGAATWGACGG primer S-*-Univ-1392-a-A-15 (5→3)
                                   (SEQ ID NO: 3)
ACGGGCGGTGTGTRC
```

These two primers originates from the work of Klindworth et al. (Nucl Acids Res (2012) 41 (1)).

The PCR reaction is then run in a dedicated thermocycler and purification of the generated amplicons is performed with commonly available custom kits for the PCR products purification. The Nextera XT® barcodes and the Illumina adapters necessary for hybridization to the flow cell are added during the cycle-limited PCR using the Nextera XT Index kit (Illumina Inc., San Diego, USA).

The generated libraries are then purified with commonly available custom kits for PCR products purification and quantified with the KAPA SYBR® FAST Universal qPCR Kit (Kapa Biosystems, Wilmington, USA). The libraries are sequenced on the Illumina MiSeq system with the MiSeq Reagent Kit V3-600 cycles (Illumina Inc., San Diego, USA). Finally, data analysis is performed with common bioinformatics pipelines and detection of the partial 16S rRNA gene sequence (SEQ ID NO:1) of the unique *Cloacimonetes* sp. (relative abundance of the 16S rRNA gene copy numbers) is done.

Method 2: Real-time PCR with species-specific TaqMan MGB (minor groove binder) probes targeting the 16S rRNA gene. The technique consists of two PCR primers (forward and reverse, sequences as specified below) and a unique TaqMan MBG probe (sequence as specified below) specifically designed to target the partial 16S rRNA gene of a unique *Cloacimonetes*. The custom TaqMan MBG probe is designed according to the specification of the Applied Biosystems and is dually labelled. The custom probe incorporates a 5' reporter and a 3' non fluorescent quencher (NFQ). Depending on the specifications of the Real-Time system used for the assay, the 5' reporter can be selected out of the following dyes: FAM™, VIC™, TET™ and/or NED™.

Sequence of the specific PCR primers and MGB probe designed to detect the unique *Cloacimonetes* sp., by targeting its partial 16S rRNA gene sequence (SEQ ID NO: 1).

```
primer_F (5→3)
                                   (SEQ ID NO: 4)
CCTTACCCGGTCTTGACATC primer_R (5→3)
                                   (SEQ ID NO: 5)
GTAACTGGAAGCAGGGGTTG MGB probe (5→3)
                                   (SEQ ID NO: 6)
CGAGGGATCCCTCA
```

After DNA extraction, a Real-time PCR with the above species-specific primers and TaqMan MGB probe is performed, and the relative abundance of the unique *Cloacimonetes* sp. in the sample of interest is determined. Calculation of the relative abundance (relative abundance of the 16S rRNA gene copy numbers) of said unique *Cloacimonetes* sp. in the environmental sample of interest, has been done according to the common Real-Time PCR practices, e.g. by using a standard curve method. Cloned partial 16S rRNA gene sequence of the unique *Cloacimonetes* sp. can be used as a template.

Total microbial abundance in the environmental sample can be calculated using standard bacterial domain-specific 16S rRNA gene-targeting PCR primers and/or probes (i.e. using the primer pair S-D-Bact-0909-a-S-18 and S-*-Univ-1392-a-A-15 with the sequences as described above, or any other commonly used universal bacterial primer pair targeting 16S rRNA gene sequence). Standard curve method and any template DNA containing the 16S rRNA gene(s) of bacterial origin in known quantity can be used to calculate the total microbial abundance (total abundance of the 16S rRNA gene copy numbers).

Example 1: Enrichment of the Biological Sample

Figure 2A:
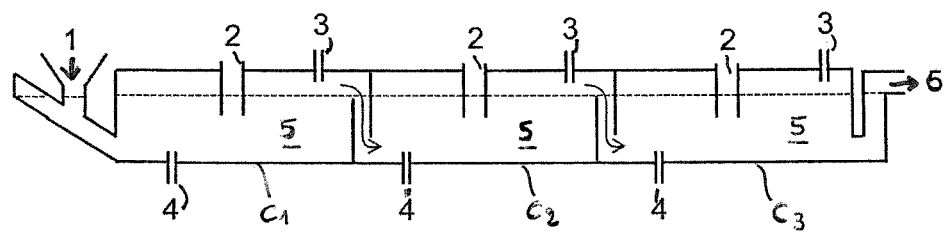
FIGS. 2A and 2B are schematic examples of reactors for enrichment of a biological sample comprising unique *Cloacimonetes* sp., respectively with three or two compartments.

The biological starting sample of this example contains said unique *Cloacimonetes* sp in abundance of at least 0.01%, preferably 0.05% of total microorganisms abundance in the source sludge, identified and determined by Real-time PCR with species-specific TaqMan MGB probes or by the 16S rRNA gene amplicon high-throughput sequencing. Said biological sample is inoculated to the reactor medium 5 at one end (inlet 1) of a horizontal anaerobic baffled reactor designed as shown in FIG. 2A having three communicating adjacent compartments c1, c2 and c3. Each compartment of 33 L is equipped with a sampling tube 2, a gas inlet 4 at the bottom for injecting oxygenated gas and a gas outlet 3 at the top part of the reactor. Substrate is introduced at one end (inlet 1) of the reactor and the enriched sludge is collected at the opposite end (outlet 6) of the reactor. This reactor is operated at mesophilic temperature range (30-40° C., preferably 37±3° C.) and fed with a pectin/cellulose/hemicellulose-rich substrate (e.g. organic domestic or industrial food waste) at high organic loading rates (OLR; 4-10 kg VS $m^{-3}.d^{-1}$, preferably in the range 6-8 kg VS $m^{-3}.d^{-1}$) and optionally supplemented with propionate (up to a final concentration in the sludge in a range of 1500-3000 mg of propionate per kg of sludge).

Figure 2B:
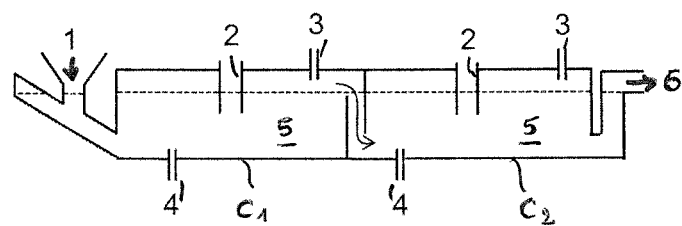

In another embodiment shown on FIG. 2B, the reactor has only two compartments c1 and c2, resulting in a shorter residence time of the sludge and a less enriched sample.

The reactor medium 5 is mixed at regular time intervals (e.g. 5 min every 2 h) with injections of gas. This gas is an oxygenated biogas: a mixture of biogas and air at the ratio of 90:10 v/v. Regular monitoring of the enrichment of said unique *Cloacimonetes* sp. with appropriate molecular tools (as specified above), up to at least 10%, preferably 25%, more preferably 30-50%, of the total microorganisms abundance in the mixture. A water-based biological agent/composition (mainly *Cloacimonetes*-enriched culture) of the invention is then obtained.

Figure 1:
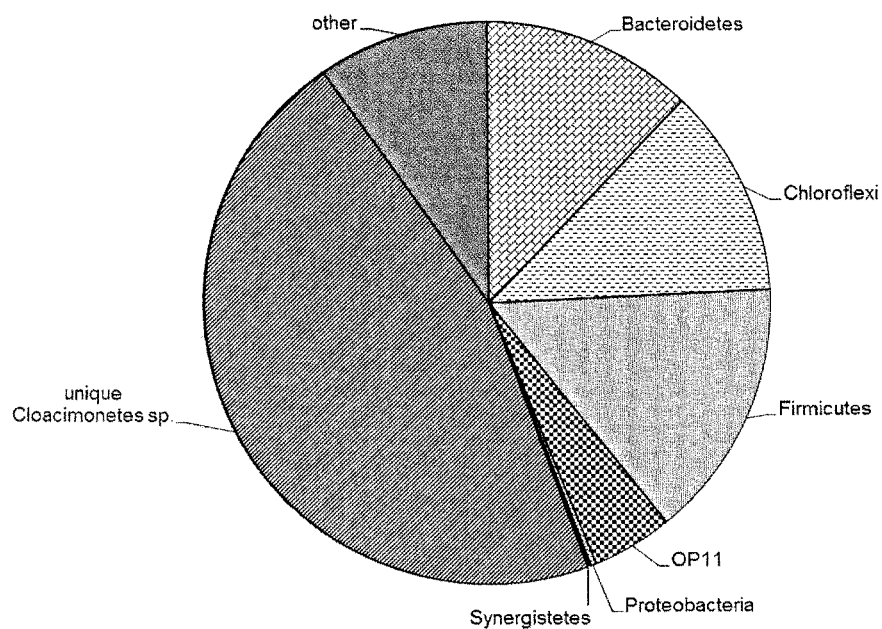
FIG. 1 illustrates an example of the biological agent of the invention showing the relative abundance of microorganisms comprising said unique *Cloacimonetes* sp.

An example of said agent is presented in FIG. 1: the major abundance (above 40%) is this unique *Cloacimonetes* sp. having a 16S rRNA gene signature comprising (SEQ ID NO:1). This bacterium has never been isolated in a pure culture, therefore it has never before been included in any microbial cocktail (bio-augmentation microbial mixture) used to recover the process of an anaerobic digestion reactors. The agent also includes the identified microorganisms Bacterioidetes, Chloroflexi, Firmicutes and smaller abundance of OP11, Proteobacteria and Synergistetes which are typical microorganisms, commonly described in anaerobic digestion reactors. Its pH is in the neutral range.

This biological agent/composition may be frozen (for example at −20° C.) or lyophilized for long-term preservation of the biological agent.

Example 2: Bio-Augmentation of an Anaerobic Digestion Reactor

The biological agent prepared above was used to bio-augment an anaerobic digestion reactor which suffered acidosis (pH under 5) as shown in diagrams C and D of FIG. 3. Bio-augmentation was done on day 70 (see arrow on diagrams D and F) in one reactor (diagrams on the right side of FIG. 3)

Diagram B presents the relationship between the abundance of said unique *Cloacimonetes* sp. and the re-establishment of a stable biogas production and shows the relative abundance of said unique *Cloacimonetes* sp. towards other dominant bacterial phyla in the *Cloacimonetes*-enriched anaerobic digestion reactor (B, bio-augmented with the biological agent started at day 70) compared to the control reactor (A, not bio-augmented with the biological agent). It can be noted that pH started immediately to increase (D) and propionate concentration was reduced. Comparison of diagrams E and F shows that the biogas composition which contains only 20% of methane in the control reactor (left), is above 50% in the bio-augmented (right) reactor, and stable for a long time, up to day 132.

REMARK: The unique *Cloacimonetes* sp. was not present at all in the control reactor but another *Cloacimonetes* representative of the *Cloacimonetes* phylum was present at day 1 in this reactor. No beneficial properties similar to those discovered with the unique *Cloacimonetes* sp. present in the biological agent were observed in the control reactor, indicating the importance of said unique *Cloacimonetes* sp. in re-establishing a stable biogas production after acidosis.

As opposed to previous studies, that were performed using small serum bottles of 160 mL capacity, the present invention proposes an efficient scaled-up preparation method of the complete microbial agent in 100 L scale reactors. Moreover, the addition to the acidified reactor of the biological agent enriched in a unique *Cloacimonetes* sp. (up to 10% v/v) was shown to restore the pH in around 10 days (pH from around 4.5 to 7-8) and the production process of a failed anaerobic digestion reactor in less than seven days (increased methane production started before the pH was completely restored to the neutral level, FIGS. 3D and F).

FIG. 4 presents a comparison of the resulting methane productivity in two anaerobic digestion reactors of different size (100 L vs. 33 L) fed with the same absolute amount of pectin/cellulose-rich substrate (resulting OLR was therefore around three times higher in the 33 L reactor). The reactor of 33 L capacity was bio-augmented with the biological agent as prepared above at day 60 (arrow). The 100 L working volume reactor was not augmented with said biological composition.

The results show increased methane productivity (NL $CH_4$ $L^{-1}.d^{-1}$) for the 33 L working volume reactor within only 7 days after being bio-augmented with said biological agent. The methane productivity was higher by 53.38%±9.89 in comparison to the control reactor operated without the addition of the biological agent of the present invention.

Therefore, as the bacterial consortium enriched in a unique *Cloacimonetes* sp. in the biological agent is resistant to high organic overload, it can apply to smaller AD reactors fed with very high OLR (high OLRs in the range of 6-8 kg VS $m^{-3}.d^{-1}$ are typically achievable under thermophilic conditions), thus reducing the operational cost (related to reactor construction, mixing and heating).

Additionally, as the bacterial consortium in the complete biological agent operates at 37° C.±3° C., running the reactor at the mesophilic temperature range further reduces the cost and risk of ammonia intoxication (as opposed to the anaerobic digestion reactors operated at the thermophilic temperatures).

Example 3: Bio-Augmentation of Another Anaerobic Digestion Reactor

The biological composition prepared in example 1 was also used to bio-augment another anaerobic digestion reactor which suffered acidosis (pH under 5) as shown in diagram B of FIG. 5. Bio-augmentation was done on day 132 (see arrow on diagrams A, B and C of FIG. 5) in this reactor.

Diagram A of FIG. 5 presents the relationship between the abundance of said unique *Cloacimonetes* sp. and the re-establishment of a stable biogas production and show the relative abundance of said unique *Cloacimonetes* sp.

towards other dominant bacterial phyla in the *Cloacimonetes*-enriched anaerobic digestion reactor (FIG. 5 diagram A, bio-augmented with the biological agent started at day 132). It can be noted that pH started immediately to increase (FIG. 5 diagram B) and propionate concentration was reduced.

FIG. 6 presents methane productivity in said anaerobic digestion reactor of 33 L size fed with the same absolute amount of pectin/cellulose-rich substrate as the 33 L reactor in FIG. 4. The reactor of 33 L capacity was bio-augmented with the biological composition as prepared above at day 132 (arrow).

As in example 2, the amount of methane in the biogas of the bio-augmented anaerobic reactor (initially around 20%; left) increased after the bio-augmentation (above 50%; right) and remain stable for a long time, up to 168 days (diagram C of FIG. 5).

The invention claimed is:

1. A biological agent for bio-augmentation of an anaerobic digestion reactor, comprising a mixture of microorganisms including at least 10%, of abundance of a unique *Cloacimonetes* sp. of the total microorganisms abundance in said mixture, said unique *Cloacimonetes* sp. having a 16S rRNA gene signature comprising the following specific sequence:

(SEQ ID NO: 1)
AAAGGAATTGACGGGGGCCCGCACAAGCGGTGGAGCATGTGGTTTAATTCG

AAGCAACGCGAAGAACCTTACCCGGTCTTGACATCCGAGGGATCCCTCAGA

GATGGGGGAGTGCCGGCTAGCCGGAACTTCGAGACAGGTGCTGCATGGCTG

TCGTCAGCTCGTGTCGTGAGATGTTGGGTTAAGTCCCGCAACGAGCGCAAC

CCCTGCTTCCAGTTACCATCATTAAGTTGGGGACTCTGGAAGGACCGCTGC

GGTAACAACGCAGAGGAAGATGGGGACGATGTCAAGTCATCATGGTCCTTA

TGACCGGGGCTACACACGTGCTACAATGGTAGTTACAGAGGGATGCGAAGG

GGTGACCTGGAGCTAATCTCTTAAAAGCTGCCACAGTTCGGATTGAGGTCT

GCAACTCGACCTCATGAAGCAGGAATCGCTAGTAATCGCGCAACATCATGG

CGCGGTGAATACGTTCCCGGGCCTTGTACACACCGCCCGT;

wherein said mixture of microorganisms is in a lyophilized state.

2. The biological agent according to claim 1, wherein the mixture of microorganisms includes 30-50% of abundance of said unique *Cloacimonetes* sp. of the total microorganisms abundance in said mixture.

3. The biological agent according to claim 1, wherein said mixture of microorganisms comprises other microorganisms selected from the following phyla: Bacteroidetes, Firmicutes, Proteobacteria, Chloroflexi, Synergistetes, and/or Microgenomates (OP11).

4. A method for preparing the biological agent according to claim 1 comprising the following steps:
   i) identifying a suitable biological sample containing a unique *Cloacimonetes* sp., having a 16S rRNA gene signature comprising SEQ ID NO:1, in a relative abundance of at least 0.01%, of the total microorganisms abundance of the sample,
   ii) inoculating the reactor medium of an anaerobic digestion reactor with the identified biological sample containing said unique *Cloacimonetes* sp.,
   iii) feeding said anaerobic digestion reactor medium with a carbohydrate-rich substrate at high organic loading rates (OLR) and optionally supplemented with organic acid(s),
   iv) mixing said reactor at regular time intervals and injecting oxygenated gas,
   v) monitoring the enrichment of the reactor medium in said unique *Cloacimonetes* sp. until the abundance of *Cloacimonetes* sp. reaches at least 10%, of the total microorganisms abundance in said reactor medium, to obtain the biological agent; and
   vi) freezing or lyophilizing said biological agent.

5. The method according to claim 4, wherein the organic loading rate (OLR) of the anaerobic digestion reactor is in the range of 4-10 kg volatile solids $m^{-3}d^{-1}$.

6. The method according to claim 4, wherein the carbohydrate-rich substrate is a vegetable waste, chosen among organic domestic and/or industrial food waste.

7. The method according to claim 6, wherein the carbohydrate-rich substrate is a vegetable waste chosen among sugar beet pulp, fruit pulp, cereal residues, and/or potatoes.

8. The method according to claim 7, wherein the starting biological sample is selected from the slurry contained in an anaerobic digestion reactor fed with waste water sludge, or agricultural residues, containing at least 0.01% of relative abundance of said unique *Cloacimonetes* sp.

9. The method according to claim 4, wherein the starting biological sample is selected from the slurry contained in an anaerobic digestion reactor fed with waste water sludge, or agricultural residues, containing at least 0.01% of relative abundance of said unique *Cloacimonetes* sp.

10. The method according to claim 4, wherein a preservative agent is added to the biological agent obtained at step v).

11. The method according to claim 4, wherein the unique *Cloacimonetes* sp., having a 16S rRNA gene signature comprising SEQ ID NO:1, is in a relative abundance of at least 0.05%, of the total microorganisms abundance of the sample.

12. The method according to claim 11, wherein the organic loading rate (OLR) of the anaerobic digestion reactor is in the range of 4-10 kg volatile solids $m^{-3}d^{-1}$.

13. A process for preventing or reducing acidosis in an anaerobic digestion reactor, in order to improve or re-establish the performance of said first reactor, comprising bio-augmenting said reactor with the biological agent according to claim 1.

14. The process according to claim 13, wherein the process consists of the bio-augmentation step.

15. The process according to claim 13, wherein the bio-augmentation step increases the organic loading rate (OLR) of said anaerobic digestion reactor.

16. The process according to claim 15, wherein the anaerobic digestion reactor produces methane.

17. The process according to claim 15, wherein the anaerobic digestion reactor produces methane under mesophilic digestion.

18. The process according to claim 13, wherein the bio-augmentation step increases the production yield of said anaerobic digestion reactor.

19. The process according to claim 18, wherein the anaerobic digestion reactor produces methane.

\* \* \* \* \*